United States Patent
Goredema et al.

(10) Patent No.: US 9,056,998 B2
(45) Date of Patent: Jun. 16, 2015

(54) CRYSTALLINE COMPOUNDS FOR PHASE CHANGE INKS

(71) Applicant: XEROX CORPORATION, Norwalk, CT (US)

(72) Inventors: Adela Goredema, Mississauga (CA); Guerino Sacripante, Oakville (CA); Kentaro Morimitsu, Mississauga (CA); Naveen Chopra, Oakville (CA); Stephan V. Drappel, Toronto (CA)

(73) Assignee: XEROX CORPORATION, Norwalk, CT (US)

( * ) Notice: Subject to any disclaimer, the term of this patent is extended or adjusted under 35 U.S.C. 154(b) by 1 day.

(21) Appl. No.: 14/053,569

(22) Filed: Oct. 14, 2013

(65) Prior Publication Data

US 2015/0105579 A1    Apr. 16, 2015

(51) Int. Cl.
C07C 69/76 (2006.01)
C09D 11/34 (2014.01)

(52) U.S. Cl.
CPC ................................ C09D 11/34 (2013.01)

(58) Field of Classification Search
CPC ................................ C07C 69/76; C07C 67/02
USPC .................................................. 560/80
See application file for complete search history.

(56) References Cited

U.S. PATENT DOCUMENTS

| | | | |
|---|---|---|---|
| 4,473,702 A * | 9/1984 | Seguchi | .......... 560/80 |
| 4,490,731 A | 12/1984 | Vaught | |
| 5,195,430 A | 3/1993 | Rise | |
| 5,231,135 A | 7/1993 | Machell et al. | |
| 5,389,958 A | 2/1995 | Bui et al. | |
| 5,621,022 A | 4/1997 | Jaeger et al. | |
| 6,221,137 B1 | 4/2001 | King et al. | |
| 6,472,523 B1 | 10/2002 | Banning et al. | |
| 6,476,219 B1 | 11/2002 | Duff et al. | |
| 6,576,747 B1 | 6/2003 | Carlini et al. | |
| 6,576,748 B1 | 6/2003 | Carlini et al. | |
| 6,590,082 B1 | 7/2003 | Banning et al. | |
| 6,646,111 B1 | 11/2003 | Carlini et al. | |
| 6,663,703 B1 | 12/2003 | Wu et al. | |
| 6,673,139 B1 | 1/2004 | Wu et al. | |
| 6,696,552 B2 | 2/2004 | Mayo et al. | |
| 6,713,614 B2 | 3/2004 | Carlini et al. | |
| 6,726,755 B2 | 4/2004 | Titterington et al. | |
| 6,755,902 B2 | 6/2004 | Banning et al. | |
| 6,821,327 B2 | 11/2004 | Jaeger et al. | |
| 6,958,406 B2 | 10/2005 | Banning et al. | |
| 7,053,227 B2 | 5/2006 | Jaeger et al. | |
| 7,381,831 B1 | 6/2008 | Banning et al. | |
| 7,427,323 B1 | 9/2008 | Birau et al. | |
| 8,815,000 B1 * | 8/2014 | Sacripante et al. | ........ 106/31.29 |

FOREIGN PATENT DOCUMENTS

JP                256262    *  9/1994

OTHER PUBLICATIONS

JP 256262 translation description and claims 1994.*
STN 1985.*
Burdge et al. (Esters of Naphthalenedicarboxylic Acids, J. Chem. and Eng. Data, vol. 8, No. 3, 1963).*
Klamann et al. (The preparation and Application of naphthalenedicarboxylic acids, erdoel und Kohle, vol. 15, pp. 438-441, 1962).*
Adela Goredema. U.S. Appl. No. 13/680,200, filed Nov. 19, 2012, Ester Resin Compositions, USA.
Gabriel Iftime, U.S. Appl. No. 13/457,157, filed Apr. 26, 2012, Fast Crystallizing-Amorphous Ink Compositions and Methods for Making the Same, USA.
Kentaro Morimitsu, U.S. Appl. No. 13/095,784, filed Apr. 27, 2011, Solid Ink Compositions Comprising Amorphous Esters of Tartaric Acid, USA.
Belelie, et al., U.S. Appl. 13/095,636, filed Apr. 27, 2011, Solid Ink Compositions Comprising Crystalline-Amorphous Mixtures, USA.

* cited by examiner

*Primary Examiner* — Yevegeny Valenrod
*Assistant Examiner* — Blaine G Doletski
(74) *Attorney, Agent, or Firm* — Pillsbury Winthrop Shaw Pittman LLP

(57) ABSTRACT

Novel crystalline compounds with at least two aromatic moieties for use in the phase change inks. The crystalline compound is derived from bio-renewable materials and can be used in phase change ink compositions to impart desirable ink properties. For example, the crystalline compounds provide phase change ink compositions suitable for ink jet printing, including robust printing on coated paper substrates.

2 Claims, 1 Drawing Sheet

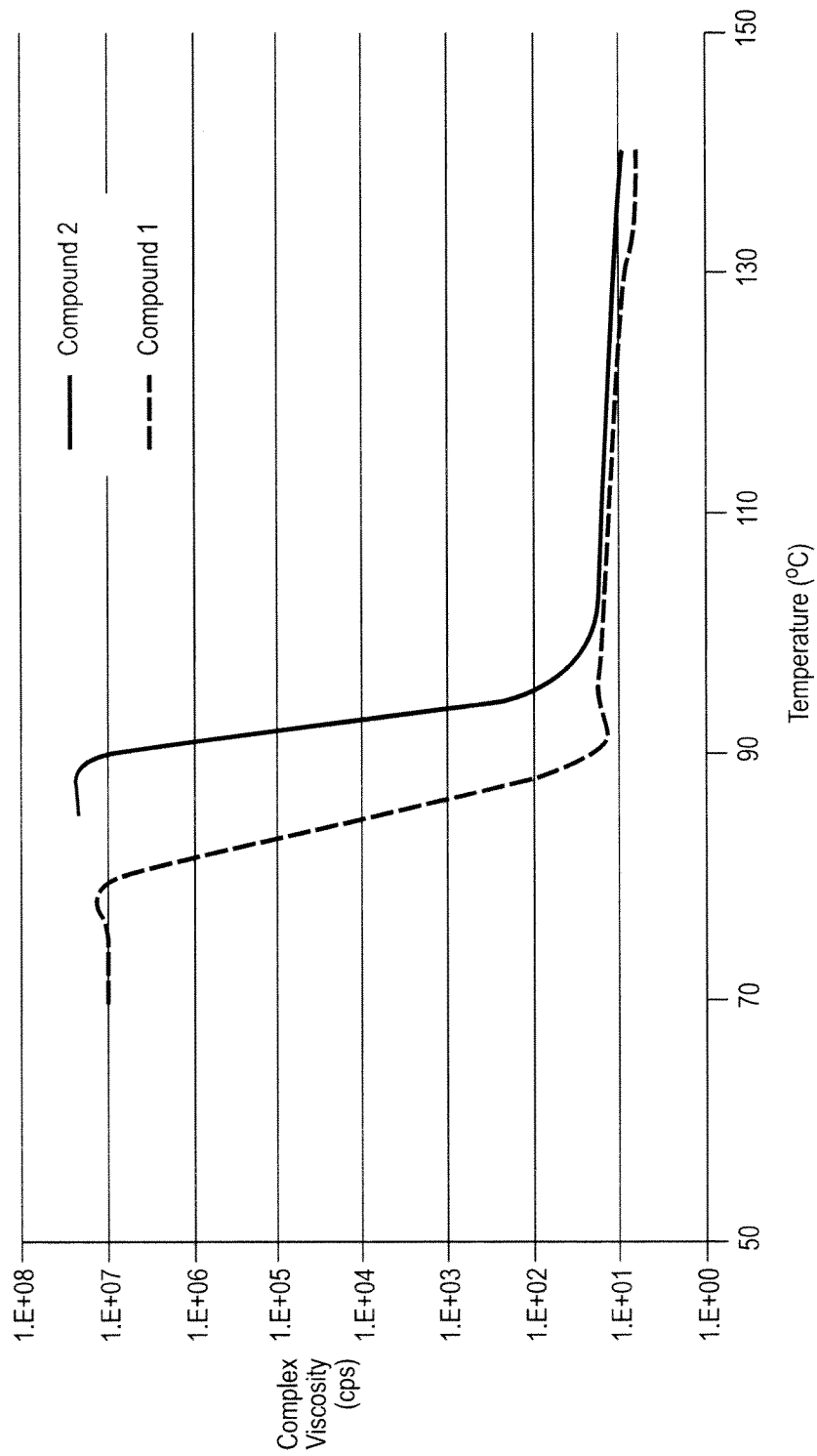

CRYSTALLINE COMPOUNDS FOR PHASE CHANGE INKS

CROSS REFERENCE TO RELATED APPLICATIONS

U.S. patent application Ser. No. 14/052,865, filed electronically on the same day as the present application, entitled "Phase Change Ink Containing Amorphous Amides," having the named inventors Naveen Chopra, Adela Goredema, Kentaro Morimitsu, Barkev Keoshkerian, Jennifer L. Belelie, and Gabriel Iftime,"

U.S. patent application Ser. No. 14/052,873, filed electronically on the same day as the present application, entitled "Amorphous Amides," having the named inventors Naveen Chopra, Adela Goredema, Kentaro Morimitsu, Barkev Keoshkerian, and Jennifer L. Belelie, U.S. patent application Ser. No. 14/053,592, filed electronically on the same day as the present application, entitled "Phase Change Inks Comprising Novel Crystalline Compounds," having the named inventors Adela Goredema, Guerino Sacripante, Barkev Keoshkerian, Daryl Vanbesien, Kentaro Morimitsu, Naveen Chopra and Gabriel Iftime, U.S. patent application Ser. No. 14/053,601, filed electronically on the same day as the present application, entitled "Bio-renewable Phase Change Inks," having the named inventors Adela Goredema, Jennifer Belelie, James Mayo, Daryl Vanbesien, Barkev Keoshkerian, Nathan Bamsey and Jenny Eliyahu, the entire disclosure of which is incorporated herein by reference in its entirety.

BACKGROUND

The present embodiments relate to phase change ink compositions characterized by being solid at room temperature and molten at an elevated temperature at which the molten ink is applied to a substrate. These phase change ink compositions can be used for ink jet printing. The present embodiments are directed to a novel phase change ink composition comprising an amorphous compound, a crystalline compound, and optionally a colorant, and methods of making the same. The specific formulations described herein, including a combination of an amorphous compound and crystalline compound which have low compatibility and are derived from bio-renewable materials and provide fast crystallizing and robust ink compositions that form high quality images when printed on coated paper substrates. In particular, the present embodiments provide novel crystalline compounds with at least two aromatic moieties for use in the phase change inks.

Ink jet printing processes may employ inks that are solid at room temperature and liquid at elevated temperatures. Such inks may be referred to as solid inks, hot melt inks, phase change inks and the like. For example, U.S. Pat. No. 4,490,731, the disclosure of which is totally incorporated herein by reference, discloses an apparatus for dispensing phase change ink for printing on a recording medium such as paper. In piezo ink jet printing processes employing hot melt inks, the phase change ink is melted by the heater in the printing apparatus and utilized (jetted) as a liquid in a manner similar to that of conventional piezo ink jet printing. Upon contact with the printing recording medium, the molten ink solidifies rapidly, enabling the colorant to substantially remain on the surface of the recording medium instead of being carried into the recording medium (for example, paper) by capillary action, thereby enabling higher print density than is generally obtained with liquid inks. Advantages of a phase change ink in ink jet printing are thus elimination of potential spillage of the ink during handling, a wide range of print density and quality, minimal paper cockle or distortion, and enablement of indefinite periods of nonprinting without the danger of nozzle clogging, even without capping the nozzles.

In general, phase change inks (sometimes referred to as "hot melt inks" or "solid inks") are in the solid phase at ambient temperature, but exist in the liquid phase at the elevated operating temperature of an ink jet printing device. At the jetting temperature, droplets of liquid ink are ejected from the printing device and, when the ink droplets contact the surface of the recording medium, either directly or via an intermediate heated transfer belt or drum, they quickly solidify to form a predetermined pattern of solidified ink drops.

Phase change inks for color printing typically comprise a phase change ink carrier composition which is combined with a phase change ink compatible colorant. In a specific embodiment, a series of colored phase change inks can be formed by combining ink carrier compositions with compatible subtractive primary colorants. The subtractive primary colored phase change inks can comprise four component dyes or pigments, namely, cyan, magenta, yellow and black, although the inks are not limited to these four colors. These subtractive primary colored inks can be formed by using a single dye or pigment or a mixture of dyes or pigments.

Phase change inks are desirable for ink jet printers because they remain in a solid phase at room temperature during shipping, long term storage, and the like. In addition, the problems associated with nozzle clogging as a result of ink evaporation with liquid ink jet inks are largely eliminated, thereby improving the reliability of the ink jet printing. Further, in phase change ink jet printers wherein the ink droplets are applied directly onto the final recording medium (for example, paper, transparency material, and the like), the droplets solidify immediately upon contact with the recording medium, so that migration of ink along the printing medium is prevented and dot quality is improved.

While the above conventional phase change ink technology is generally successful in producing vivid images and providing economy of jet use and substrate latitude on porous papers, such technology has not been satisfactory for coated substrates. For example, commercially available phase change inks also suffer from poor adhesion to coated substrates, which leads to poor scratch resistance and image robustness. Such inks also suffer from some of the hard and brittle starting materials from which they are made. This leads to the ink themselves becoming hard and brittle which exacerbates the poor substrate adhesion by causing poor "paper fold" performance and document offset. Thus, while known compositions and processes are suitable for their intended purposes, a need remains for additional means for forming images or printing on coated paper substrates. As such, there is a need to find alternative compositions, preferably those derived from bio-renewable sources, for phase change ink compositions and future printing technologies to provide customers with excellent image quality on all substrates. There is further a need to provide such phase change ink compositions which are suitable for fast printing environments like production printing.

Each of the foregoing U.S. patents and patent publications are incorporated by reference herein. Further, the appropriate components and process aspects of the each of the foregoing U.S. patents and patent publications may be selected for the present disclosure in embodiments thereof.

SUMMARY

According to embodiments illustrated herein, there is provided novel phase change ink compositions comprising an amorphous and crystalline material with limited compatibility, and a dye or an organic pigment, which are suitable for ink jet high speed printing, such as printing on coated paper substrates. Furthermore, the present embodiments provide novel crystalline materials that provide the resulting phase change inks with improved scratch resistance.

In particular, the present embodiments provide a crystalline compound comprising: a crystalline component being a di-ester compound having the following structure:

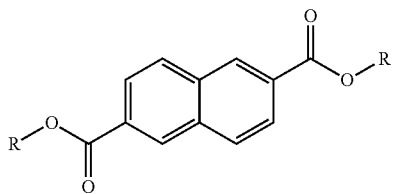

wherein R is a saturated or ethylenically unsaturated aliphatic group.

In further embodiments, there is provided a crystalline compound comprising: a dialkyl naphthalene dicarboxylate compound that is a product of the following reaction:

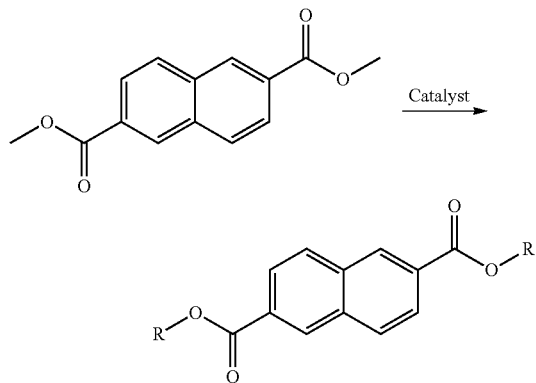

wherein R is a saturated or ethylenically unsaturated aliphatic group.

In yet other embodiments, there is provided a phase change ink component comprising: a crystalline component being a di-ester compound having the following structure:

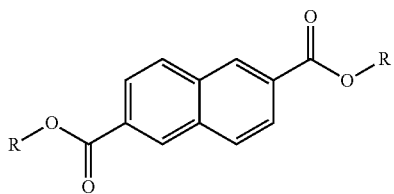

R is a saturated or ethylenically unsaturated aliphatic group.

BRIEF DESCRIPTION OF THE DRAWINGS

For a better understanding of the present embodiments, reference may be had to the accompanying FIGURE.

The FIGURE is a graph illustrating rheology data of crystalline Compound 1 made according to the present embodiments.

DETAILED DESCRIPTION

In the following description, it is understood that other embodiments may be utilized and structural and operational changes may be made without departure from the scope of the present embodiments disclosed herein.

Phase change ink technology broadens printing capability and customer base across many markets, and the diversity of printing applications will be facilitated by effective integration of printhead technology, print process and ink materials. The phase change ink compositions are characterized by being solid at room temperature (RT) (e.g., 20-27° C.) and molten at an elevated temperature at which the molten ink is applied to a substrate. As discussed above, while current ink options are successful for porous paper substrates, these options are not always satisfactory for coated paper substrates.

Conventional phase change ink technology has been successful in producing vivid images and providing economy of jet use and substrate latitude on porous papers. However, such technology has not been satisfactory for coated substrates. Thus, while known compositions and processes are suitable for their intended purposes, a need remains for additional means for forming images or printing on coated paper substrates. As such, there is a need to find alternative compositions for phase change ink compositions and future printing technologies to provide customers with excellent image quality on all substrates, including selecting and identifying different classes of materials that are suitable for use as desirable ink components. There is a further need for printing these inks at high speeds as required by digital presses in production environment.

For example, energy and environmental policies, increasing and volatile oil prices, and public/political awareness of the rapid depletion of global fossil reserves have created a need to find sustainable monomers derived from biomaterials. The present embodiments use bio-renewable materials for use in the ink compositions. The term "bio-renewable" is used to mean a material comprised of one or more monomers that are derived from plant material. By using such bio-derived feedstock, which are renewable, manufacturers may reduce their carbon footprint and move to a zero-carbon or even a carbon-neutral footprint. Bio-based materials are also very attractive in terms of specific energy and emission savings. Utilizing bio-renewable feedstock can decrease the amount of waste targeted for landfills, and reduce the economic risks and uncertainty associated with reliance on petroleum imported from unstable regions.

It was previously discovered that using a mixture of crystalline and amorphous small molecule compounds in phase change ink formulations provides robust inks, and in particular, phase change inks which demonstrate robust images on coated paper, as disclosed in U.S. patent application Ser. No. 13/095,636 to Jennifer L. Belelie et. al. filed Apr. 27, 2011, and hereby incorporated by reference in its entirety. Print samples made with such phase change inks demonstrate better robustness as compared to currently available phase change inks.

The present inventors have also found that fast crystallization of a composition made of a crystalline and an amorphous component is not an inherent property of the composition. The rate of crystallization of the crystalline/amorphous mixture is a function of not only the crystalline and amorphous components independently, but even more importantly, is influenced by the selection of the pair of crystalline and amorphous materials. For example, a given crystalline component may provide a fast crystallizing composition when mixed with one amorphous component but the same crystalline component can result in a slow crystallizing composition when mixed with a different amorphous component. The relationship between the chemical structures of the pair of crystalline and amorphous components controls the rate of crystallization of a given mixture. However, then the selection of the particular pair of crystalline and amorphous components to provide fast crystallizing inks is complicated.

The present embodiments provide a formulation for ink compositions that are based on crystalline and amorphous components which not only provide robust inks, and in particular, phase change inks which demonstrate robust images on coated paper, but further is fast crystallizing and derived from bio-renewable materials.

The present embodiments provide a new type of ink jet phase change ink composition which comprises a blend of (1) crystalline and (2) amorphous compounds, generally in a weight ratio of from about 60:40 to about 95:5, respectively. In more specific embodiments, the weight ratio of the crystalline to amorphous compound is from about 65:35 to about 95:5, or is from about 70:30 to about 90:10.

Each compound or component imparts specific properties to the phase change inks, and the resulting inks incorporating a blend of these amorphous and crystalline compounds demonstrate excellent robustness on uncoated and coated substrates. The crystalline compound in the ink formulation drives the phase change through rapid crystallization on cooling. The crystalline compound also sets up the structure of the final ink film and creates a hard ink by reducing the tackiness of the amorphous compound. The amorphous compounds provide tackiness and impart robustness to the printed ink.

U.S. patent application Ser. No. 13/457,157 to Gabriel Iftime et al., electronically filed on Apr. 26, 2012 discloses one method to achieve fast solidifying inks by using a composition wherein the crystalline and amorphous components have limited compatibility, which is hereby incorporated by reference in its entirety. By limited compatibility, it is meant that the two components have a tendency to quickly phase separate when cooled down from a molten state. Limited compatibility is achieved by selecting the crystalline and amorphous components such as to satisfy a set of design rules regarding the relationship between the functional groups present in the chemical structures of a selected pair of a crystalline and amorphous components respectively to provide the ability to rapidly crystallize. Briefly, the design rules are set forth below:

(1) The phase change ink composition comprises an amorphous compound and a crystalline compound;

(2) The amorphous compound comprises an amorphous core moiety having at least one functional group and being attached to at least one amorphous terminal group, wherein the amorphous terminal group comprises an alkyl group, wherein the alkyl is straight, branched or cyclic, saturated or unsaturated, substituted or unsubstituted, having from about 1 to about 40 carbon atoms; a diagram showing the structure of an amorphous compound is shown below:

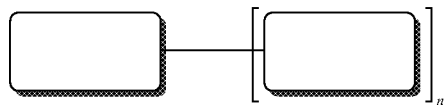

Amorphous Compound $n = 1$-$4$;

(3) The crystalline compound comprises a crystalline core moiety having at least one functional group and being attached to at least one crystalline terminal group, wherein the crystalline core group comprises an aromatic group; a diagram showing the structure of a crystalline compound is shown below:

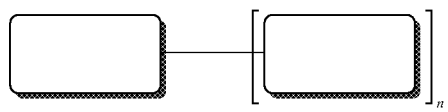

Crystalline Compound $n = 1$-$4$;

and (4) No one functional group in the amorphous core moiety is the same as any of the functional group of the crystalline core moiety.

In particular, the present embodiments use bio-renewable, fast crystallizing di-esters with at least two fused aromatic core groups and amorphous components derived from bio-renewable materials. In embodiments, the present embodiments provide inks that comprise at least 20% bio-renewable content, or from about 20 to about 85% bio-renewable content, or from about 60 to about 80%. This means that at least 20% of the ink components are derived from renewable resources such as plants. In particular, the ink compositions contain inexpensive sharp-melting crystalline materials derived from fatty monoalcohols and a dialkyl naphthalene dicarboxylates, such as dimethyl naphthalene dicarboxylate, which functions as the phase-change component, in addition to other bio-renewable materials which function as the amorphous binder resins. The fatty alcohols give the ink some hydrophobic character which helps increase ink spreadability, an improvement from other ink formulations. Moreover, the alcohols are bio-renewable and are derived from plant oils such as cotton, coconut, palm kernel, castor beans, rapeseed, soybeans and sunflowers. Thus, the crystalline materials are both inexpensive, bio-newable and biodegradable. The phase change inks made from these materials demonstrate excellent robustness compared to commercially available phase change inks on the same substrate.

In embodiments, the phase change inks meet certain specific physical properties. For example, the phase change inks of the present embodiments have a melting point ($T_{melt}$) of from about 60° C. to about 140° C. or from about 70° C. to about 130° C. In other embodiments, the ink has a crystallization temperature ($T_{crys}$) of from about 65° C. to about 110° C. or from about 70° C. to about 100° C., as determined by DSC at a rate of 10° C./min. In other embodiments, the ink of the present embodiments has a viscosity of from about 1 to about 22 cps in a jetting range of from about 100 to about 140° C. In particular, the ink of the present embodiments has a viscosity at 140° C. of <12 cps or from about 12 cps to about 3 cps, or from about 10 cps to about 5 cps. The ink may have a viscosity of greater than about $10^6$ cps at room temperature.

The Amorphous Compound

In embodiments, the amorphous compound functions as the binder agent for the crystalline component and any colorants or other minor additives. In the present embodiments, the amorphous compound is an ester compound having the general formula:

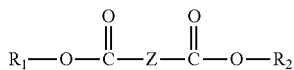

wherein $R_1$ and $R_2$ each, independently of the other, is an alkyl group, an aryl group, an arylalkyl group or a bicyclic system and Z is an alkylene group, an arylene group, an arylalkylene group, or an alkylarylene group. In specific embodiments, the amorphous compound has the structure discussed below.

Some suitable amorphous materials are disclosed in U.S. patent application Ser. No. 13/095,784 to Morimitsu et al., which is hereby incorporated by reference in its entirety. The amorphous materials may comprise an ester of tartaric acid having a formula of

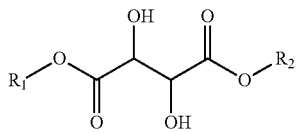

consisting of di-L-menthyl L-tartrate, di-DL-menthyl L-tartrate (DMT), di-L-menthyl DL-tartrate, di-DL-menthyl DL-tartrate, and any stereoisomers and mixtures thereof.

These materials show, relatively low viscosity ($<10^2$ centipoise (cps), or from about 1 to about 100 cps, or from about 5 to about 95 cps) near the jetting temperature ($\leq 140°$ C., or from about 100 to about $140°$ C., or from about 105 to about $140°$ C.) but very high viscosity ($>10^5$ cps) at room temperature.

To synthesize the amorphous component, tartaric acid was reacted with a variety of alcohols to make di-esters as shown in the synthesis scheme shown in U.S. patent application Ser. No. 13/095,784. Suitable alcohols to be used with the present embodiments may be selected from the group consisting of alkyl alcohol, wherein the alkyl portion of the alcohol can be straight, branched or cyclic, saturated or unsaturated, substituted or unsubstituted, having from about 1 to about 40 carbon atoms, or a substituted or unsubstituted aromatic or heteroaromatic group, and mixtures thereof. A variety of alcohols may be used in the esterification such as, for example, menthol, isomenthol, neomenthol, isoneomenthol and any stereoisomers and mixtures thereof. Mixtures of aliphatic alcohols may be used in the esterification. For example, a mixture of two aliphatic alcohols may be used in the esterification. Suitable examples of aliphatic alcohols that can be used in these mixed reactions are cyclohexanol and substituted cyclohexanols (e.g., 2-, 3- or 4-t-butyl cyclohexanol). The molar ratios of the aliphatic alcohols may be from 25:75 to 75:25, from 40:60 to 60:40, or about 50:50.

Some more suitable amorphous materials are disclosed in U.S. patent application Ser. No. 13/680,200 to Goredema et al., which is hereby incorporated by reference in its entirety.

In another embodiment, the amorphous material may comprise a di-ester having the general formula;

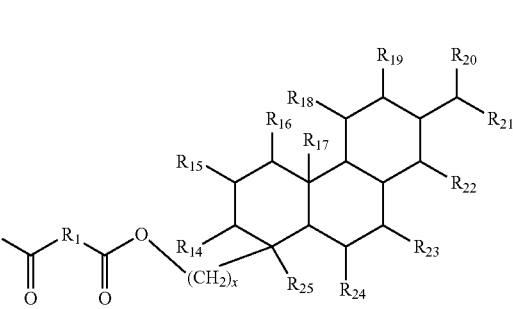

(I)

wherein $R_1$ and $R_2$ each, independently of the other or meaning that they can be the same or different, is selected from the group consisting of alkyl group, wherein the alkyl portion can be straight, branched or cyclic, saturated or unsaturated, substituted or unsubstituted, having from about 1 to about 40 carbon atoms or a substituted or unsubstituted aromatic or heteroaromatic group, and mixtures thereof. In certain embodiments, each $R_1$ and $R_2$ is independently a cyclohexyl group optionally substituted with one or more alkyl group(s) selected from methyl, ethyl, n-propyl, isopropyl, n-butyl and t-butyl.

The tartaric acid backbone is selected from L-(+)-tartaric acid, D-(−)-tartaric acid, DL-tartaric acid, or mesotartaric acid, and mixtures thereof. Depending on the R groups and the stereochemistries of tartaric acid, the esters could form crystals or stable amorphous compounds. In specific embodiments, the amorphous compound is selected from the group or

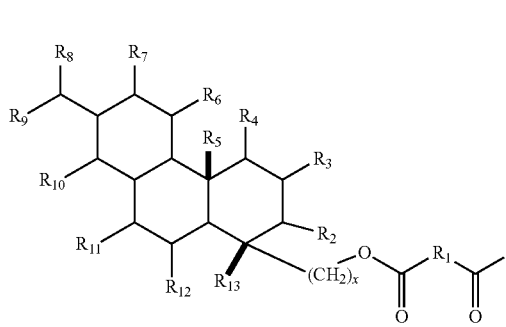

(II)

or a mixture of one or more compounds of General Formulas I and/or II;

wherein R₁ is an alkylene group, arylene group, arylalkylene group, alkylarylene group, including substituted and unsubstituted alkylene groups, and wherein hetero-atoms either may or may not be present in the alkylene group such an alkylene group containing from 2 to about 12 carbon atoms, the $R_2$-$R_{25}$ groups are independently selected from the group consisting of hydrogen, alkyl groups, arylalkyl groups, alkylaryl groups, and heterocyclic groups; wherein one or more of $R_2$-$R_{25}$ groups are included by a ring structure; and wherein (CH₂)x denotes one or more methylene groups, x an integer of from 1 to about 20 or a mixture of one or more compounds of General Formulas I and/or II.

More specifically the amorphous compound are esters of succinic acid or tartaric acid and Abitol E alcohol with the following structures;

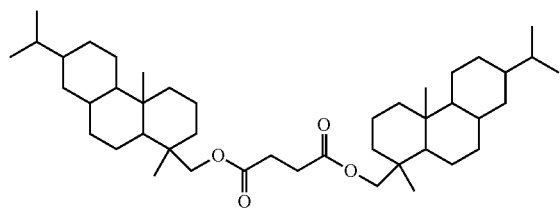 [SMILES: CC(C)C1CCC2C(CCC3C(C)(COC(=O)CCC(=O)OCC4(C)CCCC5(C)C6CCC(C(C)C)CC6CCC45)CCCC23C)C1]

or

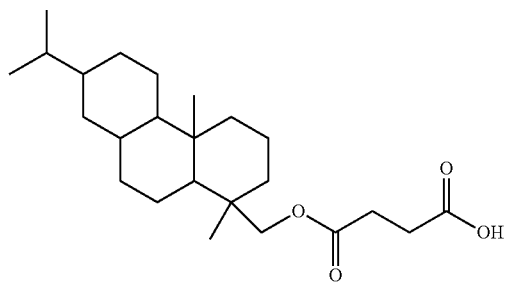 [SMILES: CC(C)C1CCC2C(CCC3C(C)(COC(=O)CCC(=O)O)CCCC23C)C1]

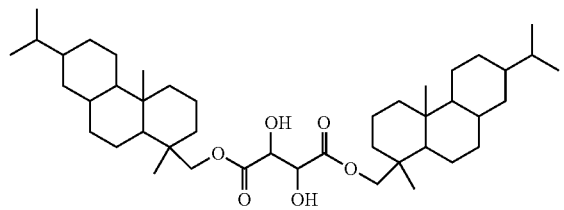 [SMILES: CC(C)C1CCC2C(CCC3C(C)(COC(=O)C(O)C(O)C(=O)OCC4(C)CCCC5(C)C6CCC(C(C)C)CC6CCC45)CCCC23C)C1]

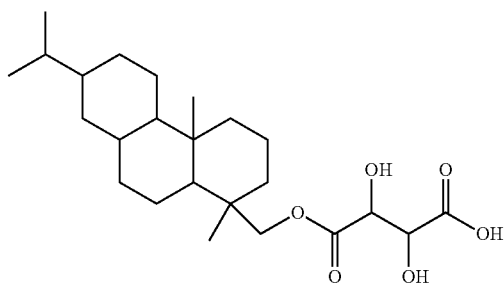 [SMILES: CC(C)C1CCC2C(CCC3C(C)(COC(=O)C(O)C(O)C(=O)O)CCCC23C)C1]

To synthesize the amorphous component, succinic acid or tartaric acid was reacted with ABITOL E™ alcohol (available from Hercules, Inc. (Wilmington, Del.)) as shown in the synthesis scheme shown in U.S. patent application Ser. No. 13/680,200 to Goredema et al. ABITOL E is shown by a representative structure, and comprises hydroabietyl alcohol (CAS[13393-93-6]), methyl ester of hydrogenated rosin (CAS[8050-15-5]), and decarboxylated rosin (CAS[8050-18-8]).

U.S. patent application Ser. No. 14/052,873 to Goredema et al. which is hereby incorporated by reference in its entirety. In specific embodiments, the amorphous material may comprise an amide having the general formula:

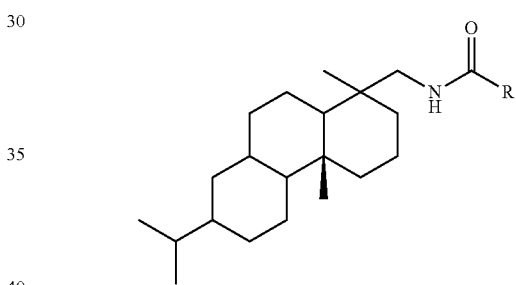

wherein R is selected from the group consisting of an alkyl group, an aryl group, an alkylaryl group, an arylalkyl group, and combinations thereof.

The amorphous amides described herein can be prepared by any suitable or desired method. In embodiments, amine D amorphous amide compounds herein are prepared by reacting amine D with an acid of the formula

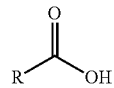

wherein R is an alkyl group having from about 1 to about 22 carbon atoms, and wherein the alkyl group can be selected from linear, branched, saturated, unsaturated, cyclic, substituted, and unsubstituted alkyl.

U.S. patent application Ser. No. 14/053,601 to Goredema et al. which is hereby incorporated by reference in its entirety.

In specific embodiments, the amorphous material can comprise an aromatic rosin ester selected from the group consisting of

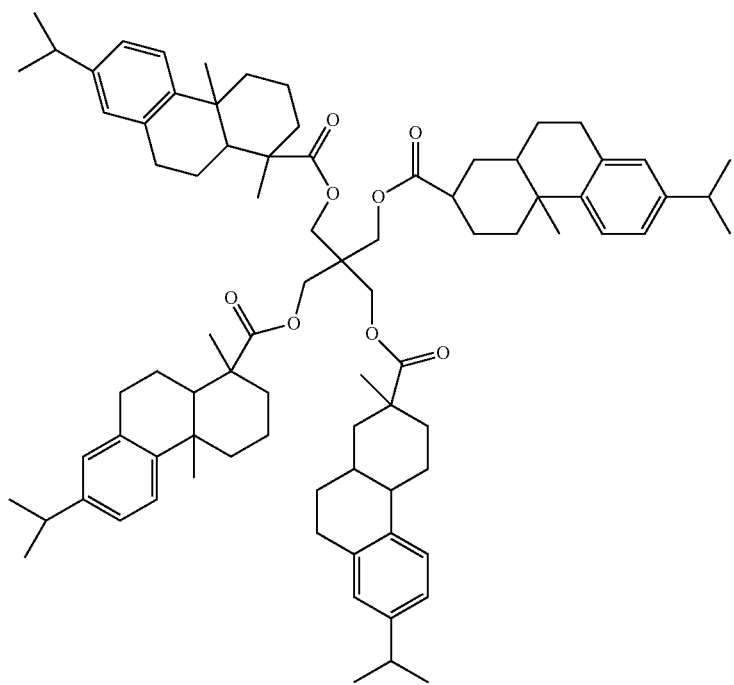 [SMILES: CC(C)c1ccc2c(c1)CCC1CC(C)(C(=O)OCC(COC(=O)C3CCC4(C)c5ccc(C(C)C)cc5CCC4C3)(COC(=O)C3(C)CCCC4(C)c5ccc(C(C)C)cc5CCC34)COC(=O)C3(C)CCCC4(C)c5ccc(C(C)C)cc5CCC34)CCC21]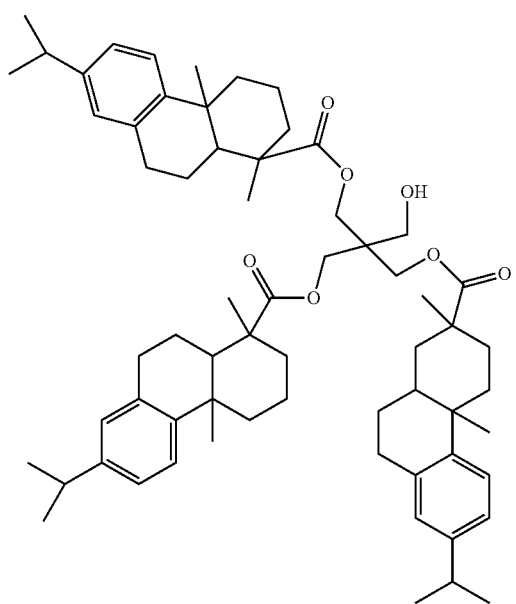 [SMILES: CC(C)c1ccc2c(c1)CCC1CC(C)(C(=O)OCC(CO)(COC(=O)C3(C)CCCC4(C)c5ccc(C(C)C)cc5CCC34)COC(=O)C3(C)CCCC4(C)c5ccc(C(C)C)cc5CCC34)CCC21C]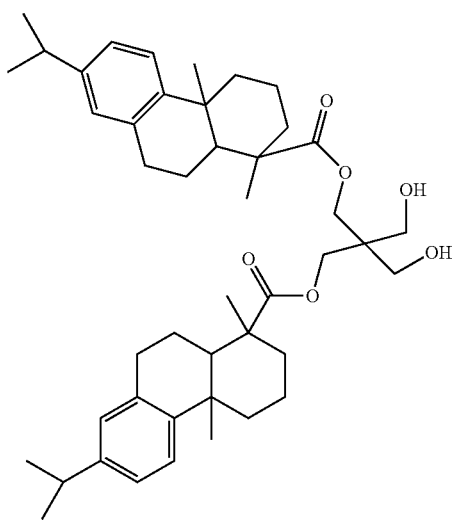 [SMILES: CC(C)c1ccc2c(c1)CCC1C(C)(C(=O)OCC(CO)(CO)COC(=O)C3(C)CCCC4(C)c5ccc(C(C)C)cc5CCC34)CCCC21C]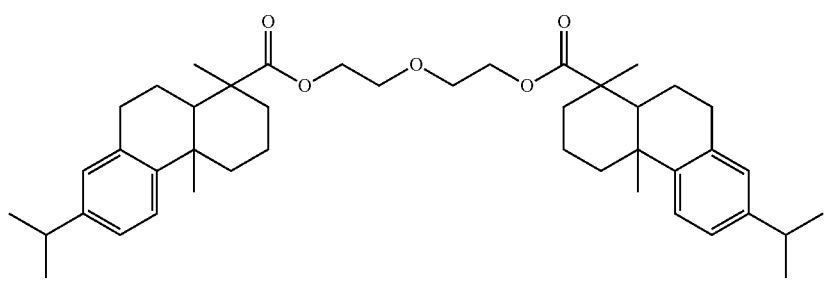 [SMILES: CC(C)c1ccc2c(c1)CCC1C(C)(C(=O)OCCOCCOC(=O)C3(C)CCCC4(C)c5ccc(C(C)C)cc5CCC34)CCCC21C]

and mixtures thereof. In further embodiments, the amorphous component comprises a mixture of

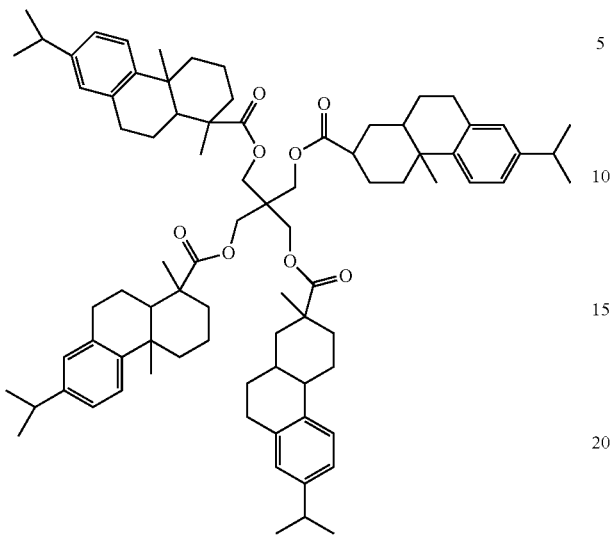

in a range of from about 5% to about 15%, or from about 5% to about 10%, percent by weight of the total weight of the amorphous component,

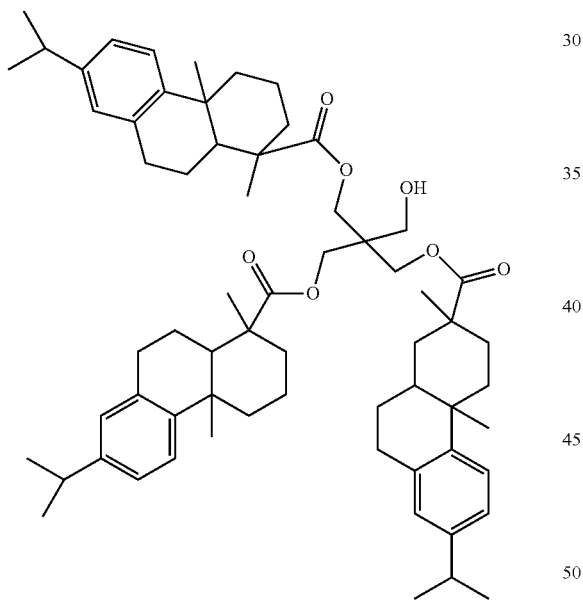

in a range of from about 1% to about 6%, or from about 1% to about 3%, percent by weight of the total weight of the amorphous component,

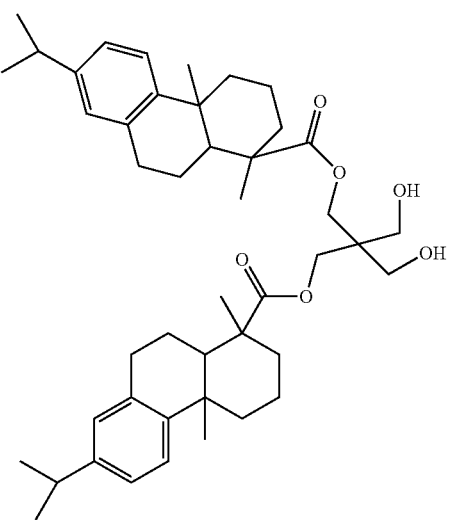

in a range of from about 3% to about 8%, or from about 4% to about 6%, percent by weight of the total weight of the amorphous component, and

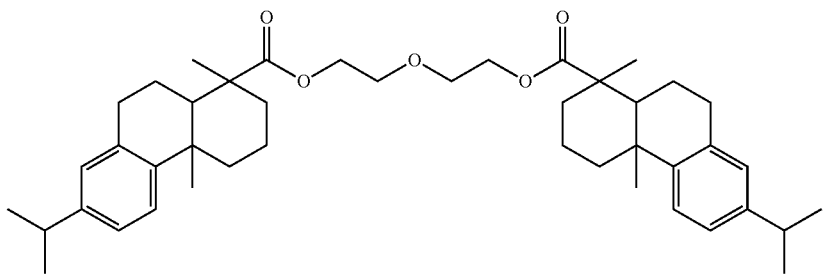

in a range of from about 75% to about 90%, or from about 75% to about 85%, percent by weight of the total weight of the amorphous component.

U.S. patent application Ser. No. 13/095,784 to Morimitsu et al., which is hereby incorporated by reference in its entirety. In another specific embodiment, the amorphous binder is an ester of Abitol E and succinic acid di-ester (Compound 3 shown in Table 1 below). Abitol E is a resin derived from pine sap and bio-based succinic acid available from corn or sorghum. The bio-renewable content is based on the weight percent of bio-based materials. Compound 3 is disclosed in U.S. patent application Ser. No. 13/680,200 to Goredema et al. which is hereby incorporated by reference in its entirety. Compound 4 is an amide derived from Amine D, a terpenoid compound derived from dehydroabeitic acid as the backbone material and which is commercially available from Eastman Chemicals Co. (Kingsport, Tenn.). In another specific embodiment, the amorphous binder is an amide of amine D available from Eastman Chemical Company and hexanoic acid (Compound 4 in Table shown in Table 1). Compound 4 is disclosed in U.S. patent application Ser. No. 14/052,873 to Goredema et al. which is hereby incorporated by reference in its entirety. Compound 5 is a rosin-based binder commercially available from Arizona Chemicals (Jacksonville, Fla.). In yet another specific embodiment, the amorphous binder is an aromatic rosin-based binder commercially available from Arizona Chemicals Jacksonville, Fla. (compound 5 shown in Table 1). Compound 5 is disclosed in U.S. patent application Ser. No. 14/053,601 to Goredema et al. which is hereby incorporated by reference in its entirety.

TABLE 1

| Compound | Structure | Bio-renewable Content (%) |
| --- | --- | --- |
| 1 | *Dimenthyl Tartrate (DMT) | 27-100* |
| 2 | *t-Butylcyclohexyl-cyclohexyl Tartrate (TBCT) | 30 |
| 3 | Abitol E Succinic Acid Di-ester | 100 |

TABLE 1-continued

| Compound | Structure | Bio-renewable Content (%) |
|---|---|---|
| 4 | 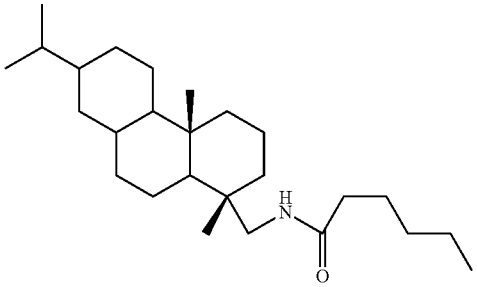<br>Amine D Hexaenoic Acid Diamide | 71 |
| 5 | 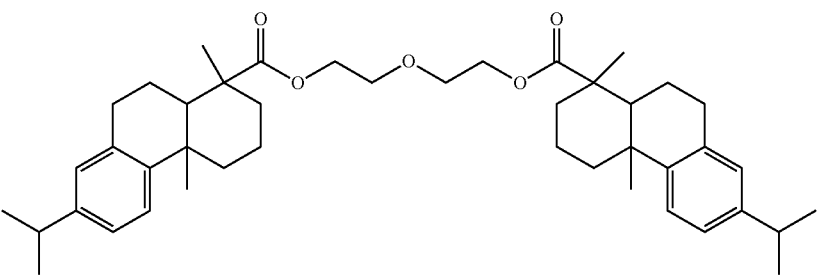<br>Sylvatac RE 40 | 80 |

*BRC depends on menthol source

The amorphous compounds show relatively low viscosity (<$10^2$ centipoise (cps), or from about 1 to about 100 cps, or from about 5 to about 95 cps) near the jetting temperature (≤140° C.) but very high viscosity (>$10^5$ cps) at room temperature.

In embodiments, the amorphous compounds are formulated with a crystalline compound to form a phase change ink composition. All of the crystalline components and some of the binders are esters. This class of materials is well known to be readily biodegradable. The ink compositions show good rheological profiles. Print samples created by the phase change ink composition on coated paper by K-proof exhibit excellent robustness.

In embodiments, the amorphous material is present in an amount of from about 5 percent to about 40 percent by weight, or from about 10 percent to about 35 percent by weight, or from about 15 percent to about 30 percent by weight of the total weight of the ink composition.

The Crystalline Compound

The novel sustainable crystalline materials of the present embodiments are synthesized from dialkyl naphthalene dicarboxylates, such as dimethyl naphthalene dicarboxylate (NDC), which is reacted with different alcohols to give di-esters with two aromatic groups in the core as shown in the scheme below.

2 R—OH +

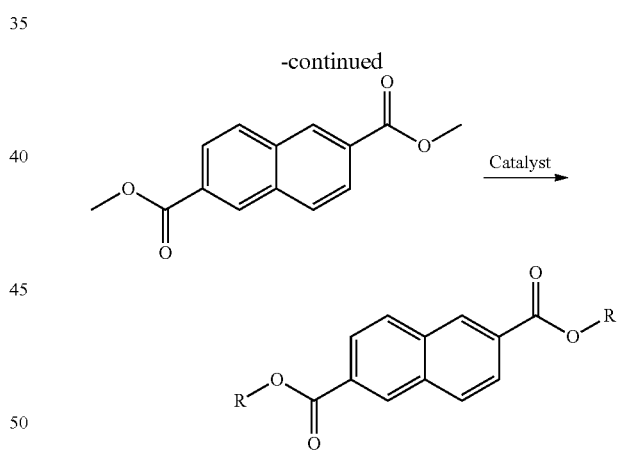

wherein R is a saturated or ethylenically unsaturated aliphatic group in one embodiment with at least about 6 carbon atoms, and in another embodiment with at least about 8 carbon atoms, and in one embodiment with no more than about 100 carbon atoms, in another embodiment with no more than about 80 carbon atoms, and in yet another embodiment with no more than about 60 carbon atoms, although the number of carbon atoms can be outside of these ranges. In a specific embodiment, the crystalline compound is derived from natural fatty alcohols such as octanol, stearyl alcohol, lauryl alcohol, behenyl alcohol, myristyl alcohol, capric alcohol, linoleyl alcohol, and mixtures thereof and the like. The above reaction may be conducted by combining dimethyl terephthalate and alcohol in the melt in the presence of a tin catalyst, such as, dibutyl tin dilaurate (Fascat 4202), dibutyl tin oxide (Fascat 4100); a zinc catalyst, such as Bi cat Z; or a bismuth catalyst, such as Bi cat 8124; Bi cat 8108, a titanium catalyst such as titanium dioxide. Only trace quantities of catalyst are required for the process.

In embodiments, the catalyst is present in an amount of about 0.01 weight percent to 2 weight percent or of about 0.05 weight percent to about 1 weight percent by weight of the total product.

The reaction is carried out at an elevated temperature of about 150° C. to about 250° C. or from about 160° C. to about 210° C. The solvent-free process is environmentally sustainable and eliminates problems with byproducts and also means higher reactor throughput.

Most of these alcohols are bio-renewable materials derived from plant oils such as cotton, coconut, palm kernel, castor beans, rapeseed, soybeans, and sunflowers. These alcohols are reacted with dimethyl naphthalene carboxylate to give the corresponding di-ester.

Examples of alcohols used in this invention include natural fatty alcohols such as stearyl alcohol, lauryl alcohol, behenyl alcohol and mixtures thereof. All of these alcohols are bio-renewable materials derived from plant oils such as cotton, coconut, palm kernel, castor beans, rapeseed, soybeans, and sunflowers.

Samples of specific alcohols for use to make the di-ester compounds (for use as the crystalline compound) were evaluated and the results are shown in Table 2. Most of the compounds showed very sharp transitions within the desirable temperature range (i.e., 60° C.<T<130° C.) indicating promising properties for the phase changing material of the ink.

TABLE 2

| Sample ID No. | R—OH | Bio-renewable Content (%)* | $T_{melt}$ (° C.) (DSC) | $T_{cryst}$ (° C.) (DSC) | Viscosity at 140° C. (cps) |
|---|---|---|---|---|---|
| Compound 1 | Stearyl alcohol $(CH_3(CH_2)_{17}OH)$ | 74 | 89 | 77 | 5.99 |
| Compound 2 | Behenyl Alcohol $(CH_3(CH_2)_{21}OH)$ | 78 | 97 | 88 | 8.67 |
| Compound 3 | Lauryl Alcohol $(CH_3(CH_2)_{11}OH)$ | 67 | — | — | — |

The bio-renewable content is based on the weight percent of bio-based materials. All of the starting materials used to make the crystalline components of the present embodiments are inexpensive. Moreover, these materials are prepared by simple, low-cost and environmentally benign synthetic routes using solventless condensation procedures with methanol as the only by-product. For example, in embodiments, the crystalline components have a bio-renewable content of at least 65 percent by weight, or from about 60 to about 85 percent by weight or from about 60 to about 80 percent by weight The crystalline materials show sharp crystallization, relatively low viscosity (≤$10^1$ centipoise (cps), or from about 0.5 to about 10 cps, or from about 1 to about 10 cps at a temperature of about 140° C., but very high viscosity (>$10^6$ cps) at room temperature. These materials have a sharp melting temperature ($T_{melt}$) of less than 150° C., or from about 65 to about 150° C., or from about 66 to about 145° C., and a sharp crystallization temperature ($T_{crys}$) of greater than 60° C., or from about 60 to about 140° C., or from about 65 to about 120° C. The ΔT between $T_{melt}$ and $T_{crys}$ is less than about 55° C.

In embodiments, the crystalline material is present in an amount of from about 60 percent to about 95 percent by weight, or from about 65 percent to about 95 percent by weight, or from about 70 percent to about 90 percent by weight of the total weight of the ink composition.

Additives

The ink of embodiments may further include conventional additives to take advantage of the known functionality associated with such conventional additives. Such additives may include, for example, at least one antioxidant, defoamer, slip and leveling agents, clarifier, viscosity modifier, adhesive, plasticizer and the like.

The ink may optionally contain antioxidants to protect the images from oxidation and also may protect the ink components from oxidation while existing as a heated melt in the ink reservoir. Examples of suitable antioxidants include N,N'-hexamethylene bis(3,5-di-tert-butyl-4-hydroxy hydrocinnamamide) (IRGANOX 1098, available from BASF); 2,2-bis (4-(2-(3,5-di-tert-butyl-4-hydroxyhydrocinnamoyloxy)) ethoxyphenyl)propane (TOPANOL-205, available from Vertellus); tris(4-tert-butyl-3-hydroxy-2,6-dimethyl benzyl)isocyanurate (Aldrich); 2,2'-ethylidene bis(4,6-di-tert-butylphenyl)fluoro phosphonite (ETHANOX-398, available from Albermarle Corporation); tetrakis(2,4-di-tert-butylphenyl)-4,4'-biphenyl diphosphonite (Aldrich); pentaerythritol tetrastearate (TCI America); tributylammonium hypophosphite (Aldrich); 2,6-di-tert-butyl-4-methoxyphenol (Aldrich); 2,4-di-tert-butyl-6-(4-methoxybenzyl)phenol (Aldrich); 4-bromo-2,6-dimethylphenol (Aldrich); 4-bromo-3,5-didimethylphenol (Aldrich); 4-bromo-2-nitrophenol (Aldrich); 4-(diethyl aminomethyl)-2,5-dimethylphenol (Aldrich); 3-dimethylaminophenol (Aldrich); 2-amino-4-tert-amylphenol (Aldrich); 2,6-bis(hydroxymethyl)-p-cresol (Aldrich); 2,2'-methylenediphenol (Aldrich); 5-(diethylamino)-2-nitrosophenol (Aldrich); 2,6-dichloro-4-fluorophenol (Aldrich); 2,6-dibromo fluoro phenol (Aldrich); α-trifluoro-o-cresol (Aldrich); 2-bromo-4-fluorophenol (Aldrich); 4-fluorophenol (Aldrich); 4-chlorophenyl-2-chloro-1,1,2-trifluoroethyl sulfone (Aldrich); 3,4-difluoro phenylacetic acid (Adrich); 3-fluorophenylacetic acid (Aldrich); 3,5-difluoro phenylacetic acid (Aldrich); 2-fluorophenylacetic acid (Aldrich); 2,5-bis(trifluoromethyl)benzoic acid (Aldrich); ethyl-2-(4-(4-(trifluoromethyl)phenoxy)phenoxy)propionate (Aldrich); tetrakis (2,4-di-tert-butyl phenyl)-4,4'-biphenyl diphosphonite (Aldrich); 4-tert-amyl phenol (Aldrich); 3-(2H-benzotriazol-2-yl)-4-hydroxy phenethylalcohol (Aldrich); NAUGARD 76, NAUGARD 445, NAUGARD 512, and NAUGARD 524 (manufactured by Chemtura Corporation); and the like, as well as mixtures thereof. The antioxidant, when present, may be present in the ink in any desired or effective amount, such as from about 0.25 percent to about 10 percent by weight of the ink or from about 1 percent to about 5 percent by weight of the ink.

Colorants

In embodiments, the phase change ink compositions described herein also include a colorant. The ink of the present embodiments can thus be one with or without colorants. The phase change ink may optionally contain colorants such as dyes or pigments. The colorants can be either from the cyan, magenta, yellow, black (CMYK) set or from spot colors obtained from custom color dyes or pigments or mixtures of pigments. Dye-based colorants are miscible with the ink base composition, which comprises the crystalline and amorphous components and any other additives.

In embodiments, the phase change ink compositions described herein also include a colorant. Any desired or effective colorant can be employed in the phase change ink compositions, including dyes, pigments, mixtures thereof, and the like, provided that the colorant can be dissolved or dispersed in the ink carrier. Any dye or pigment may be chosen, provided that it is capable of being dispersed or dissolved in the ink carrier and is compatible with the other ink components. The phase change carrier compositions can be used in combination with conventional phase change ink colorant materials, such as Color Index (C.I.) Solvent Dyes, Disperse Dyes, modified Acid and Direct Dyes, Basic Dyes, Sulphur Dyes, Vat Dyes, and the like. Examples of suitable dyes include Neozapon Red 492 (BASF); Orasol Red G (Pylam Products); Direct Brilliant Pink B (Oriental Giant Dyes); Direct Red 3BL (Classic Dyestuffs); Supranol Brilliant Red 3BW (Bayer AG); Lemon Yellow 6G (United Chemie); Light Fast Yellow 3G (Shaanxi); Aizen Spilon Yellow C-GNH (Hodogaya Chemical); Bemachrome Yellow GD Sub (Classic Dyestuffs); Cartasol Brilliant Yellow 4GF (Clariant); Cibanone Yellow 2G (Classic Dyestuffs); Orasol Black RLI (BASF); Orasol Black CN (Pylam Products); Savinyl Black RLSN (Clariant); Pyrazol Black BG (Clariant); Morfast Black 101 (Rohm & Haas); Diaazol Black RN (ICI); Thermoplast Blue 670 (BASF); Orasol Blue GN (Pylam Products); Savinyl Blue GLS (Clariant); Luxol Fast Blue MBSN (Pylam Products); Sevron Blue 5GMF (Classic Dyestuffs); Basacid Blue 750 (BASF); Keyplast Blue (Keystone Aniline Corporation); Neozapon Black X51 (BASF); Classic Solvent Black 7 (Classic Dyestuffs); Sudan Blue 670 (C.I. 61554) (BASF); Sudan Yellow 146 (C.I. 12700) (BASF); Sudan Red 462 (C.I. 26050) (BASF); C.I. Disperse Yellow 238; Neptune Red Base NB543 (BASF, C.I. Solvent Red 49); Neopen Blue FF-4012 (BASF); Fatsol Black BR (C.I. Solvent Black 35) (Chemische Fabriek Triade BV); Morton Morplas Magenta 36 (C.I. Solvent Red 172); metal phthalocyanine colorants such as those disclosed in U.S. Pat. No. 6,221,137, the disclosure of which is totally incorporated herein by reference, and the like. Polymeric dyes can also be used, such as those disclosed in, for example, U.S. Pat. No. 5,621,022 and U.S. Pat. No. 5,231,135, the disclosures of each of which are herein entirely incorporated herein by reference, and commercially available from, for example, Milliken & Company as Milliken Ink Yellow 869, Milliken Ink Blue 92, Milliken Ink Red 357, Milliken Ink Yellow 1800, Milliken Ink Black 8915-67, uncut Reactint Orange X-38, uncut Reactint Blue X-17, Solvent Yellow 162, Acid Red 52, Solvent Blue 44, and uncut Reactint Violet X-80.

Pigments are also suitable colorants for the phase change inks. Examples of suitable pigments include PALIOGEN Violet 5100 (BASF); PALIOGEN Violet 5890 (BASF); HELIOGEN Green L8730 (BASF); LITHOL Scarlet D3700 (BASE); SUNFAST Blue 15:4 (Sun Chemical); Hostaperm Blue B2G-D (Clariant); Hostaperm Blue B4G (Clariant); Permanent Red P-F7RK; Hostaperm Violet BL (Clariant); LITHOL Scarlet 4440 (BASF); Bon Red C (Dominion Color Company); ORACET Pink RF (BASF); PALIOGEN Red 3871 K (BASF); SUNFAST Blue 15:3 (Sun Chemical); PALIOGEN Red 3340 (BASF); SUNFAST Carbazole Violet 23 (Sun Chemical); LITHOL Fast Scarlet L4300 (BASF); SUNBRITE Yellow 17 (Sun Chemical); HELIOGEN Blue L6900, L7020 (BASF); SUNBRITE Yellow 74 (Sun Chemical); SPECTRA PAC C Orange 16 (Sun Chemical); HELIOGEN Blue K6902, K6910 (BASF); SUNFAST Magenta 122 (Sun Chemical); HELIOGEN Blue D6840, D7080 (BASF); Sudan Blue OS (BASF); NEOPEN Blue FF4012 (BASF); PV Fast Blue B2GO1 (Clariant); IRGALITE Blue GLO (BASF); PALIOGEN Blue 6470 (BASF); Sudan Orange G (Aldrich); Sudan Orange 220 (BASF); PALIOGEN Orange 3040 (BASF); PALIOGEN Yellow 152, 1560 (BASF); LITHOL Fast Yellow 0991 K (BASF); PALIOTOL Yellow 1840 (BASF); NOVOPERM Yellow FGL (Clariant); Ink Jet Yellow 4G VP2532 (Clariant); Toner Yellow HG (Clariant); Lumogen Yellow D0790 (BASF); Suco-Yellow L1250 (BASF); Suco-Yellow D1355 (BASF); Suco Fast Yellow D1355, D1351 (BASF); HOSTAPERM Pink E 02 (Clariant); Hansa Brilliant Yellow 5GX03 (Clariant); Permanent Yellow GRL 02 (Clariant); Permanent Rubine L6B 05 (Clariant); FANAL Pink D4830 (BASF); CINQUASIA Magenta (DU PONT); PALIOGEN Black L0084 (BASF); Pigment Black K801 (BASF); and carbon blacks such as REGAL 330™ (Cabot), Nipex 150 (Evonik) Carbon Black 5250 and Carbon Black 5750 (Columbia Chemical), and the like, as well as mixtures thereof.

Pigment dispersions in the ink base may be stabilized by synergists and dispersants. Generally, suitable pigments may be organic materials or inorganic. Magnetic material-based pigments are also suitable, for example, for the fabrication of robust Magnetic Ink Character Recognition (MICR) inks. Magnetic pigments include magnetic nanoparticles, such as for example, ferromagnetic nanoparticles.

Also suitable are the colorants disclosed in U.S. Pat. No. 6,472,523, U.S. Pat. No. 6,726,755, U.S. Pat. No. 6,476,219, U.S. Pat. No. 6,576,747, U.S. Pat. No. 6,713,614, U.S. Pat. No. 6,663,703, U.S. Pat. No. 6,755,902, U.S. Pat. No. 6,590,082, U.S. Pat. No. 6,696,552, U.S. Pat. No. 6,576,748, U.S. Pat. No. 6,646,111, U.S. Pat. No. 6,673,139, U.S. Pat. No. 6,958,406, U.S. Pat. No. 6,821,327, U.S. Pat. No. 7,053,227, U.S. Pat. No. 7,381,831 and U.S. Pat. No. 7,427,323, the disclosures of each of which are incorporated herein by reference in their entirety.

In embodiments, solvent dyes are employed. An example of a solvent dye suitable for use herein may include spirit soluble dyes because of their compatibility with the ink carriers disclosed herein. Examples of suitable spirit solvent dyes include Neozapon Red 492 (BASF); Orasol Red G (Pylam Products); Direct Brilliant Pink B (Global Colors); Aizen Spilon Red C-BH (Hodogaya Chemical); Kayanol Red 3BL (Nippon Kayaku); Spirit Fast Yellow 3G; Aizen Spilon Yellow C-GNH (Hodogaya Chemical); Cartasol Brilliant Yellow 4GF (Clariant); Pergasol Yellow 5RA EX (Classic Dyestuffs); Orasol Black RLI (BASF); Orasol Blue GN (Pylam Products); Savinyl Black RLS (Clariant); Morfast Black 101 (Rohm and Haas); Thermoplast Blue 670 (BASF); Savinyl Blue GLS (Sandoz); Luxol Fast Blue MBSN (Pylam); Sevron Blue 5GMF (Classic Dyestuffs); Basacid Blue 750 (BASF); Keyplast Blue (Keystone Aniline Corporation); Neozapon Black X51 (C.I. Solvent Black, C.I. 12195) (BASF); Sudan Blue 670 (C.I. 61554) (BASF); Sudan Yellow 146 (C.I. 12700) (BASF); Sudan Red 462 (C.I. 260501) (BASF), mixtures thereof and the like.

The colorant may be present in the phase change ink in any desired or effective amount to obtain the desired color or hue such as, for example, at least from about 0.1 percent by weight of the ink to about 50 percent by weight of the ink, at least from about 0.2 percent by weight of the ink to about 20 percent by weight of the ink, and at least from about 0.5 percent by weight of the ink to about 10 percent by weight of the ink.

The ink compositions can be prepared by any desired or suitable method. For example, each of the components of the ink carrier can be mixed together, followed by heating, the mixture to at least its melting point, for example from about 60° C. to about 150° C., 80° C. to about 145° C. and 85° C. to about 140° C. The colorant may be added before the ink ingredients have been heated or after the ink ingredients have been heated. When pigments are the selected colorants, the molten mixture may be subjected to grinding in an attritor or media mill apparatus to effect dispersion of the pigment in the ink carrier. The heated mixture is then stirred for about 5 seconds to about 30 minutes or more, to obtain a substantially homogeneous, uniform melt, followed by cooling the ink to ambient temperature (typically from about 20° C. to about 25° C.). The inks are solid at ambient temperature. The inks can be employed in apparatus for direct printing ink jet processes and in indirect (offset) printing ink jet applications. Another embodiment disclosed herein is directed to a process which comprises incorporating an ink as disclosed herein into an ink jet printing apparatus, melting the ink, and causing droplets of the melted ink to be ejected in an imagewise pattern onto a recording substrate. A direct printing process is also disclosed in, for example, U.S. Pat. No. 5,195,430, the disclosure of which is totally incorporated herein by reference. Yet another embodiment disclosed herein is directed to a process which comprises incorporating an ink as disclosed herein into an ink jet printing apparatus, melting the ink, causing droplets of the melted ink to be ejected in an imagewise pattern onto an intermediate transfer member, and transferring the ink in the imagewise pattern from the intermediate transfer member to a final recording substrate. In a specific embodiment, the intermediate transfer member is heated to a temperature above that of the final recording sheet and below that of the melted ink in the printing apparatus. In another specific embodiment, both the intermediate transfer member and the final recording sheet are heated; in this embodiment, both the intermediate transfer member and the final recording sheet are heated to a temperature below that of the melted ink in the printing apparatus; in this embodiment, the relative temperatures of the intermediate transfer member and the final recording sheet can be (1) the intermediate transfer member is heated to a temperature above that of the final recording substrate and below that of the melted ink in the printing apparatus; (2) the final recording substrate is heated to a temperature above that of the intermediate transfer member and below that of the melted ink in the printing apparatus; or (3) the intermediate transfer member and the final recording sheet are heated to approximately the same temperature. An offset or indirect printing process is also disclosed in, for example, U.S. Pat. No. 5,389,958, the disclosure of which is totally incorporated herein by reference. In one specific embodiment, the printing apparatus employs a piezoelectric printing process wherein droplets of the ink are caused to be ejected in imagewise pattern by oscillations of piezoelectric vibrating elements. Inks as disclosed herein can also be employed in other hot melt printing processes, such as hot melt acoustic ink jet printing, hot melt thermal ink jet printing, hot melt continuous stream or deflection ink jet printing, and the like. Phase change inks as disclosed herein can also be used in printing processes other than hot melt ink jet printing processes.

Any suitable substrate or recording sheet can be employed, including plain papers such as XEROX 4200 papers, XEROX Image Series papers, Courtland 4024 DP paper, ruled notebook paper, bond paper, silica coated papers such as Sharp Company silica coated paper, JuJo paper, HAMMERMILL LASERPRINT paper, and the like, glossy coated papers such as XEROX Digital Color Elite Gloss, Sappi Warren Papers LUSTROGLOSS, specialty papers such as Xerox DURAPAPER, and the like, transparency materials, fabrics, textile products, plastics, polymeric films, inorganic recording mediums such as metals and wood, and the like, transparency materials, fabrics, textile products, plastics, polymeric films, inorganic substrates such as metals and wood, and the like.

The inks described herein are further illustrated in the following examples. All parts and percentages are by weight unless otherwise indicated.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

While the description above refers to particular embodiments, it will be understood that many modifications may be made without departing from the spirit thereof. The accompanying claims are intended to cover such modifications as would fall within the true scope and spirit of embodiments herein.

The presently disclosed embodiments are, therefore, to be considered in all respects as illustrative and not restrictive, the scope of embodiments being indicated by the appended claims rather than the foregoing description. All changes that come within the meaning of and range of equivalency of the claims are intended to be embraced therein.

EXAMPLES

The examples set forth herein below and are illustrative of different compositions and conditions that can be used in practicing the present embodiments. All proportions are by weight unless otherwise indicated. It will be apparent, however, that the present embodiments can be practiced with many types of compositions and can have many different uses in accordance with the disclosure above and as pointed out hereinafter.

Example 1

Synthesis of distearyl naphthalene-2,6-dicarboxylate (Compound 1, Table 2)

To a 3 neck 100 mL round bottomed flask equipped with a Dean Stark trap and condenser, thermocouple and argon inlet was added dimethyl naphthalene-2,6-dicarboxylate (10 grams, 40.94 mmoles, available from Sigma Aldrich), stearyl alcohol (22.15 grams, 81.89 mmoles, available from Spectrum Chemical), Fascat 4100 (0.03 grams, 0.1 wt %, available from Arkema Inc) and Xylenes (50 ml, available from Sigma Aldrich). The mixture was slowly heated under argon to 160° C. during which reagents melted/dissolved. The temperature was raised to 180° C. The reaction mixture was stirred at 180° C. overnight (~20 hours) during which 46 mL of a mixture of xylenes and methanol was collected. Vacuum was applied (1-2 mm-Hg) for about 10 minutes during which an additional 5 mL of a mixture of Xylenes and methanol was collected. The solution was cooled under argon to about 140° C. and discharged in an aluminum tray where it was allowed to cool to room temperature to give product as an off-white solid. The product was transferred to a 1 L Erlenmeyer flask, about 100 mL of isopropyl alcohol was added, heated to about 100° C. during which product dissolved. The solution was cooled to room temperature during which product crystallized out, filtered and dried on a vacuum pump overnight to give 25.33 grams product as an off-white solid (86% yield). The product was shown to be pure by $^1$H NMR with trace amounts of the mono-ester. Physical properties of this compound are shown in Table 2 above. The FIGURE shows the rheological profile.

A small amount of Xylenes was used to help prevent sublimation of the dimethyl naphthalene-2,6-dicarboxylate. If the reaction is done in a pressurized reactor, the solvent will not be required.

Example 2

Synthesis of dibehenyl naphthalene-2,6-dicarboxylate (Compounds 2 Table 2)

Compound 2 was synthesized using the same procedure outlined for Compound 1 except Behenyl alcohol was used instead of stearyl alcohol and was not recrystallized. Physical properties for this compound are shown in Table 2 above. The rheological profile of Compound 2 is shown in the FIGURE. As shown in the FIGURE, both Compounds 1 and 2 have very sharp phase changes above 90° C. and low viscosity (<10 cps) in the jetting range of 100-140° C. making them suitable candidates for the robust phase change inks of the present embodiments.

Example 3

Synthesis of dilauryl naphthalene-2,6-dicarboxylate (Compound 3, Table 2)

Compound 3 was synthesized using the same procedure outlined for Compound 1 except Lauryl alcohol was used instead of stearyl alcohol.

All the starting materials used to make the crystalline components of the present embodiments are inexpensive and safe. In fact, some of the fatty alcohols are used in the pharmaceutical industry. The crystalline materials are prepared by simple, low-cost and environmentally benign synthetic routes using solventless condensation procedures with methanol as the only by-product. Dimethyl naphthalene-2,6-dicarboxylate is used for the synthesis because the melting point of Naphthalene dicarboxylate (NDC) is too high. The fatty alcohols used to make the crystalline components of the present embodiments are derived from plants giving these components, in embodiments, at least greater than 65% bio-renewable content.

Example 4

Ink Compositions

Five amorphous binders were used to make inks of the present embodiments, as shown in Table 3.

Inks were formulated using mixtures of some of the novel sustainable crystalline components listed in Table 2 and amorphous binders components listed in Table 1 Table 3 shows the composition and properties of the bio-renewable and robust phase change inks made with the dialkyl naphthalene dicarboxylate crystalline materials of this invention.

TABLE 3

| | | Ink 1 | Ink 2 | Ink 3 | Ink 4 | Ink 5 |
|---|---|---|---|---|---|---|
| Crystalline material phouscom | Compound 1 (BRC = 74%) | 78.4 | 78.4 | 76.48 | 76.48 | 76.48 |
| | DMT (BRC ~27-100%) | | 19.6 | | | |
| | TBCT (30% BRC) | | | | 19.12 | |
| | Abitol E SA (BRC ~100%) | 19.6 | | | | |
| | Sylvatac RE 40 ((BRC ~80%) | | | | 19.12 | |
| | Amine D Diamide (~71% (BRC) | | | | | 19.12 |
| Solsperse 3200 dispersant | | | | 2 | 2 | 2 |
| SunFlo SFD-B124 Synergist | | | | 0.4 | 0.4 | 0.4 |
| Keystone Solvent blue 101 Dye | | 2 | 2 | | | |
| Hostapern B4G Cyan Pigment | | | | 2 | 2 | 2 |
| Total | | 100 | 100 | 100 | 100 | 100 |
| *BRC (%) | | ~78 | ~61-78 | ~62 | ~69 | ~70 |
| **Viscosity @ 140° C. (cps) | | 7.28 | 6.25 | 12.09 | 10.23 | 7.98 |
| Tcryst. (° C.) (by rheology) | | 80 | 80 | 80 | 80 | 80 |

*Bio-renewable content-weight percent of bio-based materials
**Frequency = 1 Hz; 25 mm parallel plate geometry; gap = 0.2 mm; strain % = 400%

Evaluation of Ink Robustness

Inks 1-5 were printed onto DCEG coated papers (120 gsm stock) using a K-proofer gravure printing plate, which was rigged with a pressure roll set at low pressure. The gravure plate temperature was set at 142° C., but the actual plate temperature was about 134° C. The K-proofer apparatus (manufactured by RK Print Coat Instrument Ltd., Litlington, Royston, Heris, SG8 0OZ, U.K.) is a useful printing tool to screen a variety of inks at small scale and to assess image quality on various substrates, before an ink formulation is scaled up and optimized for more in-depth inkjet printing tests.

K-proofs were fed through a Xerox PHASER 4200 printer (Saturn) at 1 inch per second (1 ips) at a drum temperature of 50° C. with the ink surface facing the oiled drum. One K-proof of each ink was then scratched using a three-finger gouge system. No ink was visibly removed from the images made with ink examples 1-5 indicating that images are robust. Another K-proof was folded along with a Xerox Business 4200 (75 gsm) facing page in a Duplo D-590 folder and evaluated for fold crease and fold offset. The folded K-proof of Inks 1-5 showed no fold crease indicating good image robustness.

SUMMARY

In summary, novel crystalline materials with two fused aromatic rings in the core were synthesized from naphthalene dicarboxylate and various bio-renewable alcohols. The alcohols used are derived from bio-renewable resources giving materials with up to 78% bio-renewable content. In addition, the crystalline materials can be synthesized using simple neat conditions. The resulting crystalline materials demonstrated physical properties desirable for robust phase change inks.

The present embodiments thus also provide sustainable and robust phase change inks with excellent scratch resistance, even on coated substrates, made from the novel crystalline materials.

The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others. Unless specifically recited in a claim, steps or components of claims should not be implied or imported from the specification or any other claims as to any particular order, number, position, size, shape, angle, color, or material.

All the patents and applications referred to herein are hereby specifically, and totally incorporated herein by reference in their entirety in the instant specification.

What is claimed is:

1. A compound having the following structure:

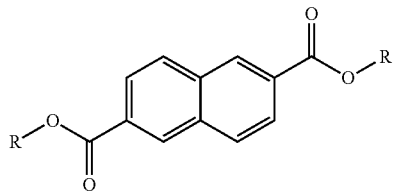

wherein R is stearyl or behenyl.

2. The compound of claim 1 wherein the compound is produced by the following reaction:

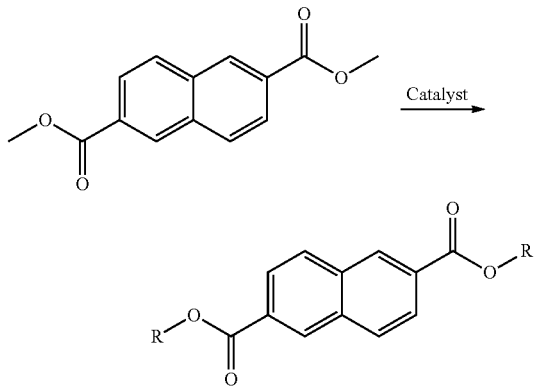

wherein R is stearyl or behenyl.

* * * * *